(12) United States Patent
Lee (10) Patent No.: US 9,107,647 B2
(45) Date of Patent: Aug. 18, 2015

(54) HEART STABILIZER

(76) Inventor: Young-Sam Lee, Geumwang-gun (KR)

( * ) Notice: Subject to any disclaimer, the term of this patent is extended or adjusted under 35 U.S.C. 154(b) by 244 days.

(21) Appl. No.: 13/823,332

(22) PCT Filed: Oct. 22, 2010

(86) PCT No.: PCT/KR2010/007270
§ 371 (c)(1),
(2), (4) Date: Mar. 14, 2013

(87) PCT Pub. No.: WO2012/053683
PCT Pub. Date: Apr. 26, 2012

(65) Prior Publication Data
US 2013/0184520 A1    Jul. 18, 2013

(30) Foreign Application Priority Data

Oct. 20, 2010    (KR) .......................... 10-2010-0102598

(51) Int. Cl.
| | |
|---|---|
| *A61F 2/00* | (2006.01) |
| *A61B 17/02* | (2006.01) |
| *A61B 17/00* | (2006.01) |
| *A61B 17/30* | (2006.01) |
| *A61B 19/00* | (2006.01) |

(52) U.S. Cl.
CPC ....... *A61B 17/02* (2013.01); *A61B 2017/00314* (2013.01); *A61B 2017/0243* (2013.01); *A61B 2017/306* (2013.01); *A61B 2019/2246* (2013.01); *A61B 2019/266* (2013.01); *A61B 2019/268* (2013.01)

(58) Field of Classification Search
CPC .................. A61B 17/02; A61B 2017/0243
USPC .................................. 600/37, 201, 205, 230
See application file for complete search history.

(56) References Cited

U.S. PATENT DOCUMENTS

| | | | |
|---|---|---|---|
| 6,464,629 B1 | 10/2002 | Boone et al. | |
| 2003/0158542 A1 | 8/2003 | Nguyen et al. | |

FOREIGN PATENT DOCUMENTS

| | | |
|---|---|---|
| KR | 20-0377123 Y1 | 3/2005 |
| KR | 10-2009-0046008 A | 5/2009 |
| KR | 10-2009-0068953 A | 6/2009 |

*Primary Examiner* — John Lacyk
(74) *Attorney, Agent, or Firm* — Jefferson IP Law, LLP

(57) ABSTRACT

Disclosed is a heart stabilizer used when a coronary artery of a heart is operated. The heart stabilizer allows an intake tube connected to a suction unit for holding the heart to perform a suctioning operation while preventing clogging in any circumstances, allows the direction of the suction unit to be converted to forward, rearward, leftward, and rightward directions, allows the angle of the suction unit to be minutely adjusted even after the suction unit is primarily fixed, and is cleaned while the suction unit maintains the adjusting function of the adjustor for adjusting and fixing the angle.

11 Claims, 11 Drawing Sheets

HEART STABILIZER

TECHNICAL FIELD

The present invention relates to a heart stabilizer which can accurately and safely raise a beating heart, fix the heart while variously converting the direction of the heart, and firmly hold the heart while easily moving the heart according to a change of the operated part during an operation, when a coronary artery of the heart is operated.

More particularly, the present invention relates to a heart stabilizer which can allow an intake tube connected to a suction unit for holding the heart to perform a suctioning operation while preventing clogging in any circumstances, allow the direction of the suction unit to be converted in forward, rearward, leftward, and rightward directions, allow the angle of the suction unit to be minutely adjusted even after the suction unit is primarily fixed, and be cleaned while the suction unit maintains the adjusting function of the adjustor for adjusting and fixing the angle.

BACKGROUND ART

A heart of a human body is a central organ of a circulation system which provides a motive power for circulating blood. The heart periodically contracts and releases repeatedly to function as a pump for supplying blood to the entire body. Heart diseases include congenital heart diseases and acquired heart diseases.

The heart diseases include various diseases such as coronary artery disease, valvular heart disease, and arrhythmias. The coronary artery disease which is most frequent in the heart diseases narrows or clogs an inner cavity of a blood vessel, causing a cardiovascular disease due to due to the coronary artery sclerosis, which makes blood circulation difficult, in spite that the coronary artery itself has a capability to sufficiently expand the inner cavity.

The arteries of the heart includes an artery for sending blood to a heart wall and supporting the heart itself and two left and right arteries, which are called a coronary artery.

The coronary artery starts from a base of an aorta extending from the heart.

If fat substances such as cholesterol are accumulated in at least one of the three artery vessels to be thicker, narrowing or clogging the blood vessels to cause a lesion, blood containing oxygen cannot be supplied to the heart. Accordingly, angina pectoris is caused due to lack of supply of blood to the heart, and myocardial infarction is caused if the coronary artery is clogged.

In recent year, in order to treat the coronary artery disease, an operation of making a detour using another artery or a vein is performed. During the heart operation, an operated part of a surface of the heart is stabilized by using a specific tool while the heart is beating and is easily operated by operating a heart stabilizer.

A method of treating and operating a heart disease includes a coronary artery replacing/planting operation, and the most important part in the planting operation is to stabilize the heart and raise the heart so that a view of field can be secured and an operation can be easily performed, allowing the clogged blood part to be treated with an artificial blood implant.

The heart stabilizer used for the operation known until now according to the related art includes a suction unit for suction and attach an epidermis of the heart, an adjustor for adjusting an angle of the suction unit, a suction head connecting the adjustor and the suction unit, a handle for manipulating fastening and releasing the adjustor, and a main holder slidably mounted to a rail of an operation table.

However, in the heart stabilizer according to the related art, when the intake tube for maintaining a suction pressure so that the suction unit can suction and raise the epidermis of the heart for an operation is twisted or bent due to an external force during an operation due to various position changes of the suction unit and left and right rotation and forward and rearward movement of the stabilizer, the suction unit is clogged, causing the heart to drop down, while not maintaining the suction pressure, which causes a serious problem.

Further, even during a suctioning operation, if the suction opening of the suction unit suctions the epidermis of the heart, the suction nozzle for suctioning air is clogged, lowering a suctioning force for holding the heart, so the heart may drop down or be moved during an operation, making it difficult to properly perform a precise heart operation.

Further, as the suction unit and the adjustor integrally adjust an angle of the suction unit when the suction unit is attached to the epidermis of the heart, the adjustor needs to be fixed through manipulation of the handle after it is released again to he adjusted through manipulation of the handle when the suction position of the heart is minutely adjusted after adjusted to a predetermined angle, which makes it impossible to minutely adjust the suction unit to a desired position.

Further, several block bodies are generally assembled in the adjustor for the operation so that the angle of the adjustor may be variously adjusted or the adjustor may be fastened or released. However, when foreign substances are introduced between the assembled block bodies, the angle cannot be easily adjusted, so a flexible vinyl covers the adjustor. The covering of the vinyl prevents foreign substance from being introduced between the assembled blocks but causes inconvenience to adjustment of various angles.

In addition, most of the heart stabilizers are imported, and the imported stabilizers are neither economical nor efficient as the structure of the suction unit, the suction head, the adjustor, the handle, or the main holder is complex and an operation thereof is neither certain nor accurate.

DISCLOSURE

Technical Problem

The present invention has been made in an effort to solve the above-described problems, and an object of the present invention is to provide a heart stabilizer which allows an angle of a suction unit to be minutely adjusted with the angle of the suction unit being fixed while preventing the suction unit from being clogged in any circumstances, and maintains a cleaned state while making an adjusting angle of the adjustor free.

The present invention also provides a heart stabilizer which can induce an accuracy of an operation thereof while simplifying the entire assembly structure, thereby replacing import and promoting export of the heart stabilizer.

Technical Solution

In order to solve these problems, according to an aspect of the present invention, there is provided a heart stabilizer, in which auxiliary gas passages recessed to an inner side of a gas passage of an intake tube connected to a suction unit are radially formed so that the intake tube is prevented from being clogged by the auxiliary gas passages even when the intake tube is bent, and which introduces a minute adjusting structure in a suction head for fixing and connecting the suction unit and the suction unit to allow the suction unit to be variously adjusted while the suction unit is fixed, and in which a flexible bellows tube is mounted to the adjustor so that the adjustor can be easily adjusted while the heart stabilizer maintains a clear state.

Further, the structures of the adjustor, the handle, and the main holder as well as the suction unit and the suction head are made simple, and the heart stabilizer can be easily manufactured and accurately operated.

Advantageous Effects

As described above, according to the present invention, auxiliary gas passages are formed in an intake tube of a suction unit used during a heart operation prevents the suction unit from accidentally dropping down from a surface of the heart as air can pass through the intake tube even when the intake tube is bent, prevents foreign substances from being introduced into an aperture of a flexible arm to secure flexibility, allows an angle of the suction unit to be minutely adjusted even when the angle of the suction unit is primarily fixed, increases stability of the operation, and secures view of field of the operated part and increases an approach to the operated part through improvement of the structure thereof, making it possible to easily perform the operation and shorten the operation time.

BEST MODE

[Mode for Invention]

The present invention provides a heart stabilizer including: a suction unit fixedly attached to a surface of a heart; a suction head connecting the suction unit and an adjustor to adjust and fix an upward, downward, leftward, and rightward movement range of the suction unit; an adjustor for fixing the adjusted state through manipulation of a handle while guiding the adjusted movement range of the suction head; a handle mounted to a rear end of the adjustor so as to be connected to the adjustor to fix the suction head as well as the adjustor through fastening and unfastening thereof; and a main holder connected to a tip end and a rear end of the handle so as to extend to the adjustor to fix the adjustor to a rail of an operating table, wherein auxiliary radial gas passages are formed on an inner wall of a gas passage of an intake tube so as to be recessed to prevent the intake tube from failing to properly perform an intake operation when the intake tube is bent during an operation due to twisting thereof generated when a position of the intake tube is changed variously.

Hereinafter, an exemplary embodiment of the present invention will be described with reference to the accompanying drawings.

As shown in FIGS. 1 to 4, the basic construction of the present invention includes: a suction unit 10 fixedly attached to a surface of a heart; a suction had 20 connecting the suction unit 10 and an adjustor 30 to adjust and fix an upward, downward, leftward, and rightward movement range of the suction unit 10; an adjustor 30 for fixing the adjusted state through manipulation of a handle 40 while guiding the adjusted movement range of the suction head 20; a handle 40 mounted to a rear end of the adjustor 30 so as to be connected to the adjustor 30 to fix the suction head 20 as well as the adjustor 30 through fastening and unfastening thereof; and a main holder 50 connected to a tip end and a rear end of the handle 40 so as to extend to the adjustor 30 to fix the adjustor 30 to a rail of an operating table.

Then, auxiliary radial gas passages 13b are formed on an inner wall of a gas passage 13a of an intake tube 13 so as to be recessed to prevent the intake tube 13 from failing to properly perform an intake operation when the intake tube 13 is bent during an operation due to twisting thereof generated when a position of the intake tube 13 is changed variously.

Figure 1:
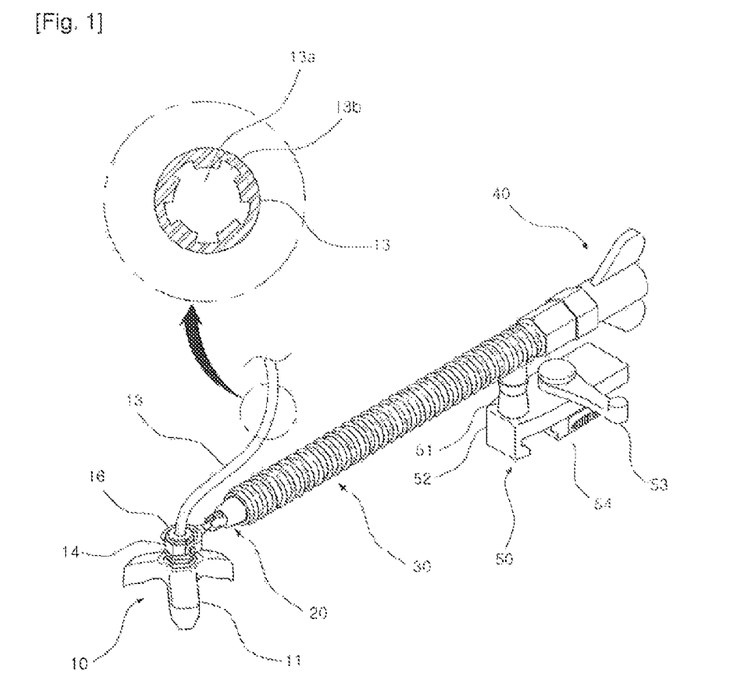
FIG. 1 is a perspective view showing an embodiment of the present invention.
Figure 2:
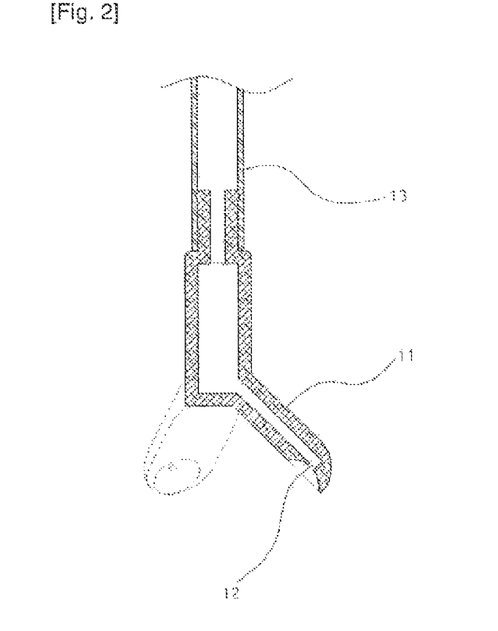
FIGS. 2 and 3 are schematic views of an embodiment of a suction unit of the present invention.

Then, as shown in FIG. 2, a suction opening 12 is formed on an inner side of a recessed opening 12-1 recessed in step to prevent clogging due to the epidermis when a suction operation is performed toward an inner side of the branch tube 11 branched to three directions so that the suction unit 10 is firmly attached to a surface of the heart through a suction operation of the intake tube 13 connected to an upper side of the suction unit 10.

Figure 3:
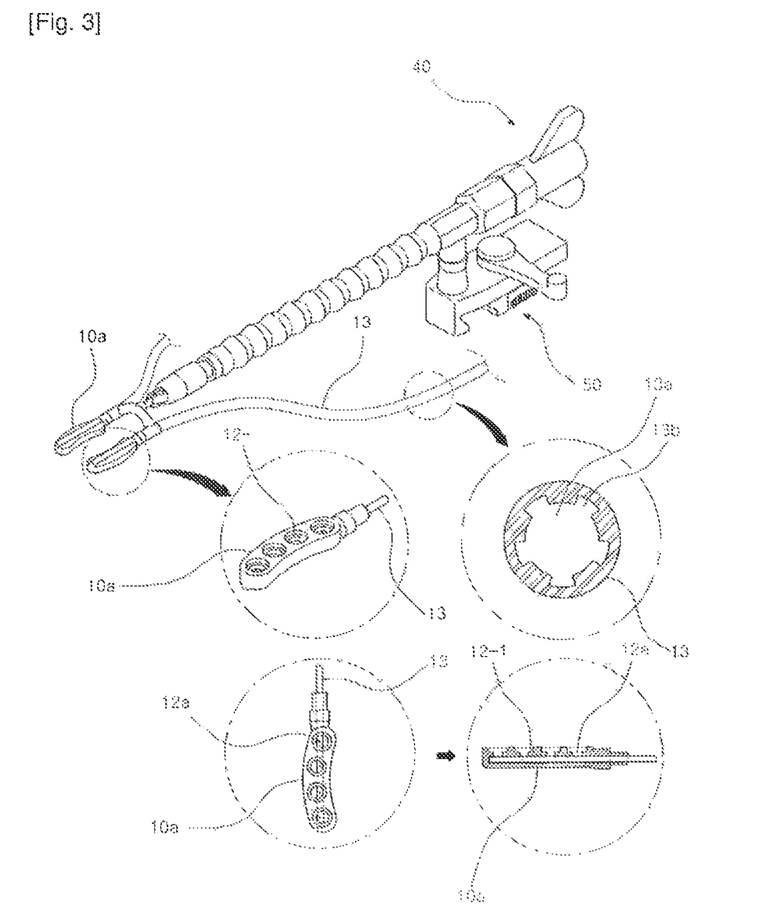

As shown in FIG. 3, another suction unit 10a is curved to one side edge in a straight shape and is curved in a state where the intake tube 13 is linearly introduced into a plurality of suction openings 12a arranged in a row so that the suction openings 12a are located at different locations of the recessed opening 12-1.

Even in this case, the recessed opening 12-1 is formed to be stepped and an intake opening is formed at an inner side thereof so that a suctioned epidermis of the heart from clogging the intake opening.

A rotary shaft 15 is formed at an upper side of the suction unit 10 and a washer 14 is fitted with the rotary shaft 15 so that the rotary shaft 15 is rotated to finely change a location at which a branch tube 11 of the suction unit 10 is attached to a surface of the heart when an angle of the suction unit 10 is adjusted by the suction head 20, and a fixing boss 14a is formed in the washer 14 after the washer 14 is fitted with the rotary shaft 15, and is inserted into a boss hole 16a of a connecting body 16 inserted into the suction head 20.

Then, the washer 14 is connected to the rotary shaft 15 by means of a separate packing 19 to prevent the washer 14 from applying a damage to the suction unit 10.

Figure 4:
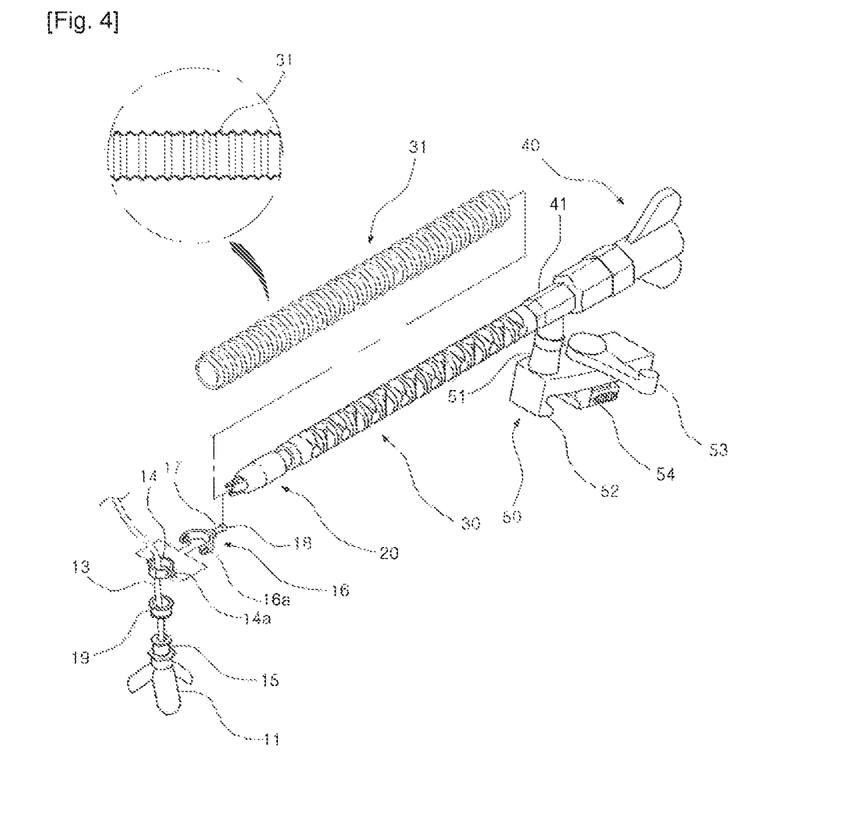
FIG. 4 is a perspective view showing a state where a bellows tube is formed in an adjustor of the present invention.

The suction head 20 connected to a connecting ball 18 of a connecting shaft 17 of the connecting body 16, which connecting shaft 17 has a predetermined length, is connected to the adjustor 30 having block bodies to adjust a bending angle of the adjustor 30 by pulling and releasing a wire 100 through manipulation of the handle 40, the adjustor 30 is configured by assembling three block bodies 32 which are coupled to each other by a vinyl cover generally contracted by heat to prevent dust from being put between assembly apertures when the adjustor 30 is exposed to the outside, and a bellows tube 31 is coupled between the suction head 20 and the main holder 50 outside the adjustor 30 to be prevented from being arbitrarily separated to prevent introduction of foreign substances so that a function of the adjustor 30 is smoothly performed by preventing dust from being put between the apertures of the block bodies constituting the adjustor 30 by using the vinyl cover to easily adjust the adjustor 30.

Figure 5:
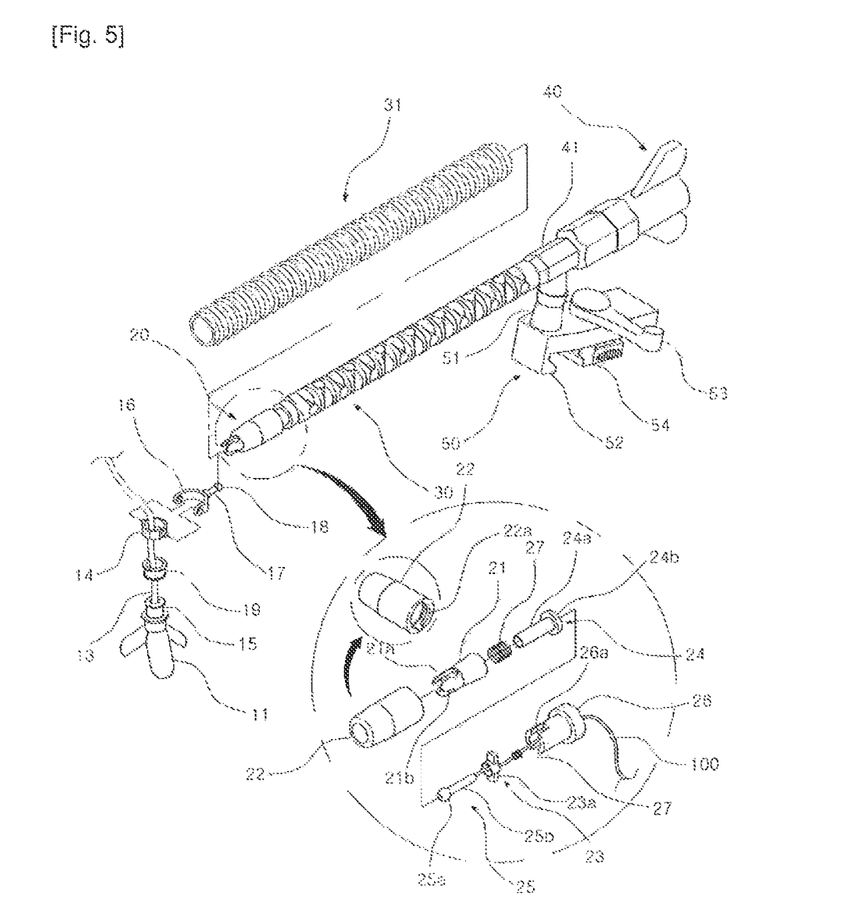
FIG. 5 is an assembled structure view of a suction head of the present invention.
Figure 6:
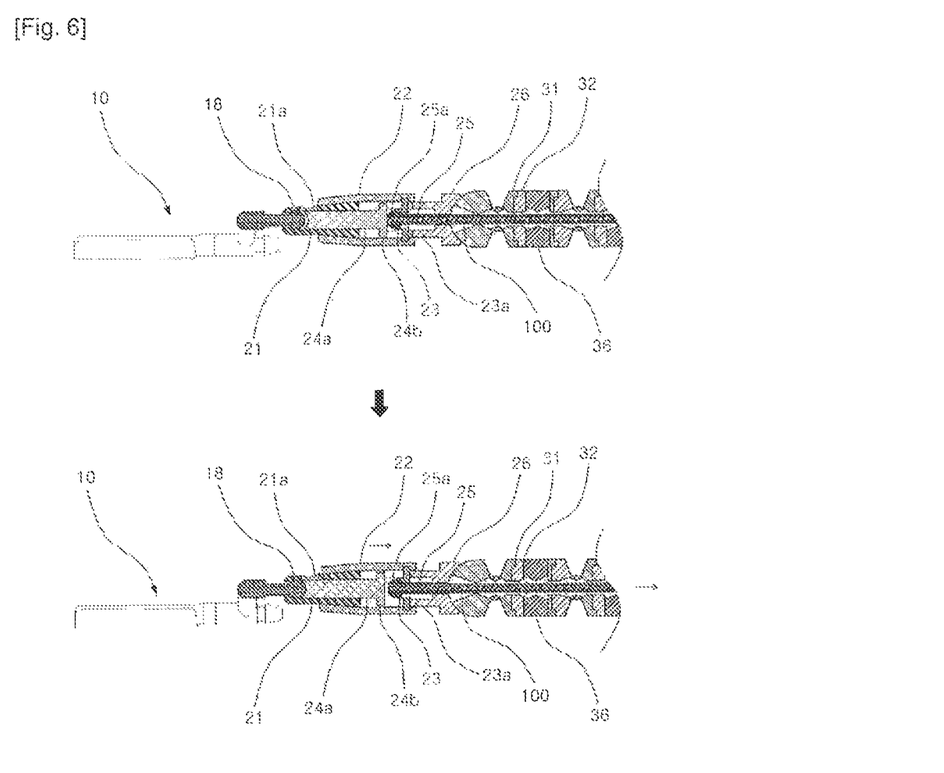
FIG. 6 is a sectional view of an operation state of the suction head of the present invention.

Then, as shown in FIGS. 5 and 6, the suction head 20 includes an accommodating cap 21 for accommodating a connecting shaft and a connecting ball of the connecting body, and the accommodating cap 21 is inserted into an operating cap 22 so that the operating cap 22 is inserted into a guide groove 26a of a fixing body 22 to be coupled to the operating body 23 which is raised or lowered, and the operating body 23 is inserted into the fixing body 26 in the state where the operating shaft 25 for pressing or releasing the pressing shaft 24 pressed and attached to the connecting rod of the connecting body.

Then, the pressing shaft 24 and the operating body 23 is pressed and released by a return spring 27, and an exposed portion 21b having a cutaway portion 21a is formed in the accommodating cap 21 inserted into the operating cap 22 to fold the connecting shaft to four sides while accommodating the connecting rod of the connecting body so that only the exposed portion is exposed to the outside of the operating cab 22.

The pressing shaft 24 pressed and released by the operating shaft 25 is classified into a shaft 24a and a flange 24b while being inserted into the accommodating cap 21 so that a tip end of the shaft 24a is firmly attached to or separated from the connecting rod of the connecting body to be pressed or released.

The operating shaft 25 has a head 25a to be attached to a lower end of the flange 24b of the pressing shaft 24, and the tubular shaft 25b is inserted into the operating body 23 so that the operating body 23 is raised and lowered in the guide groove 26a of the fixing body 26 by pulling the wire 100.

Then, slide bosses 23a are formed at opposite ends of the operating body 23, the slide bosses 23 protrude while being inserted into the guide groove 26a of the fixing body 26 to be stopped by and fixed to a stopping rim 22a of the operating cap 22 accommodating the accommodating cap 21.

Figure 7:
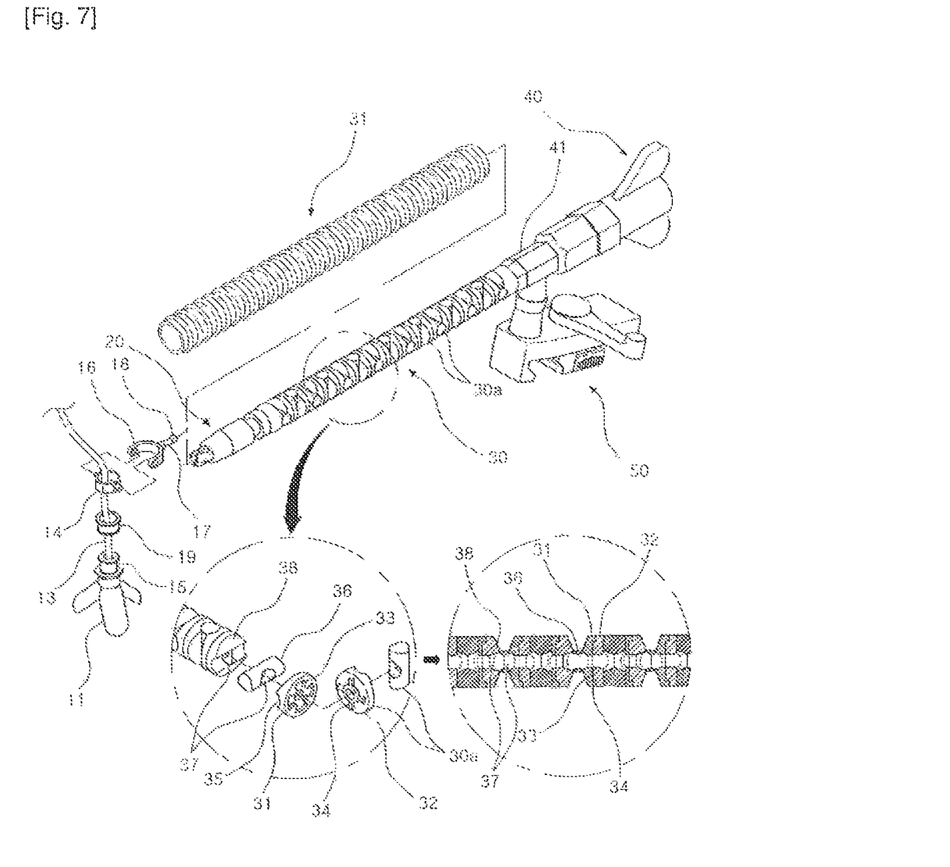
FIG. 7 is a structure view of the adjustor of the present invention.
Figure 8:
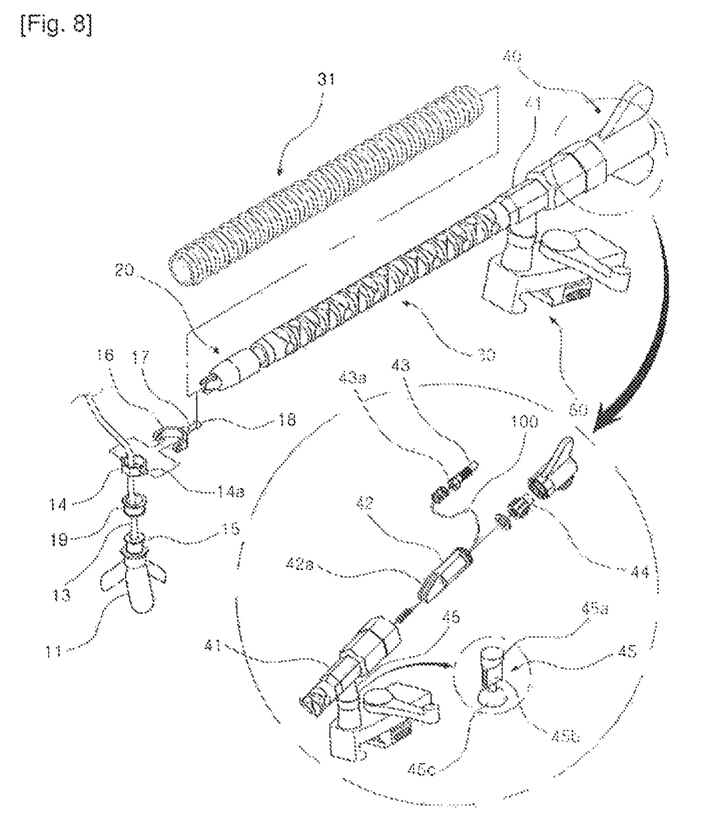
FIG. 8 is an assembled structure view of a handle of the present invention.

As shown in FIG. 7, the adjustor 30 for adjusting an angle of and fixing the suction head 20 includes disk bodies 31 and 32 side surfaces of which are engaged with each other by using recesses 33 and protrusions 34, and a cylindrical body 36 a substantially half of which is inserted into and attached to the curved recesses 35 formed on rear surfaces of the disk bodes 31 and 32. The cylindrical body 36 is continuously connected to each other between the disk bodies so that a wire 100 is connected through a hole 37 punched at a center thereof.

Then, one end of the wire 100 extends to the handle 40 located at a rear side of the main holder 50 to be fixed while being fixed to the operating shaft 25 of the suction head 20.

Inclined surfaces 38 are formed at opposite sides of the adjustor 30 such that the adjustor 30 is bent and maintained at a predetermined angle by bending the disk bodies 31 and 32 with a cylindrical body 36 while taking curved, recesses 35 formed on rear surfaces of the disk bodies 31 and 32 as borders, thereby preventing the adjustor from being bent at a predetermined angle or more during a use thereof.

Figure 9:
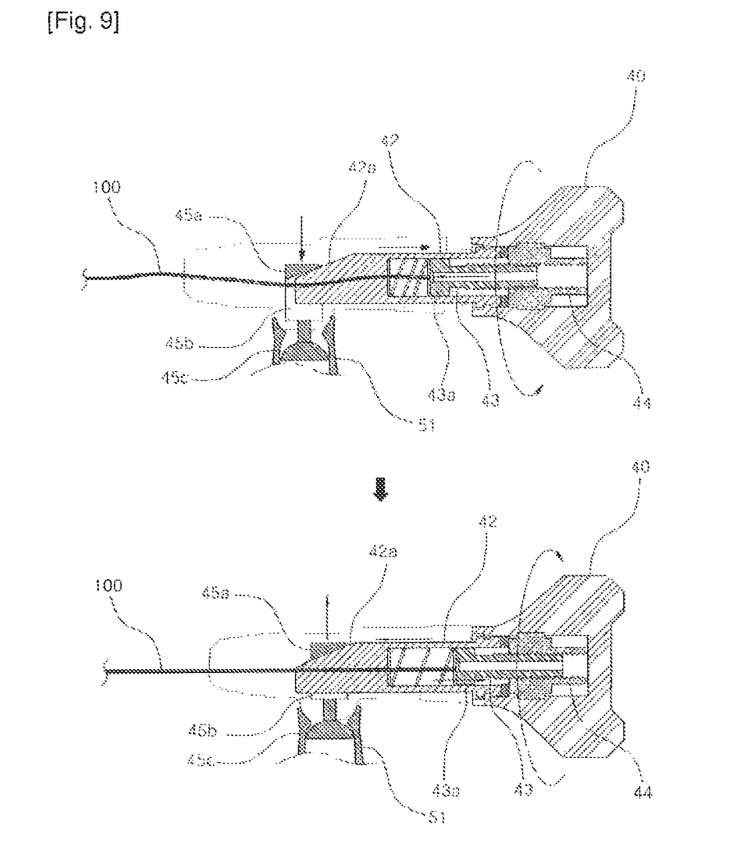
FIG. 9 is a sectional view showing an operation state according to manipulation of the handle of the present invention.
Figure 10:
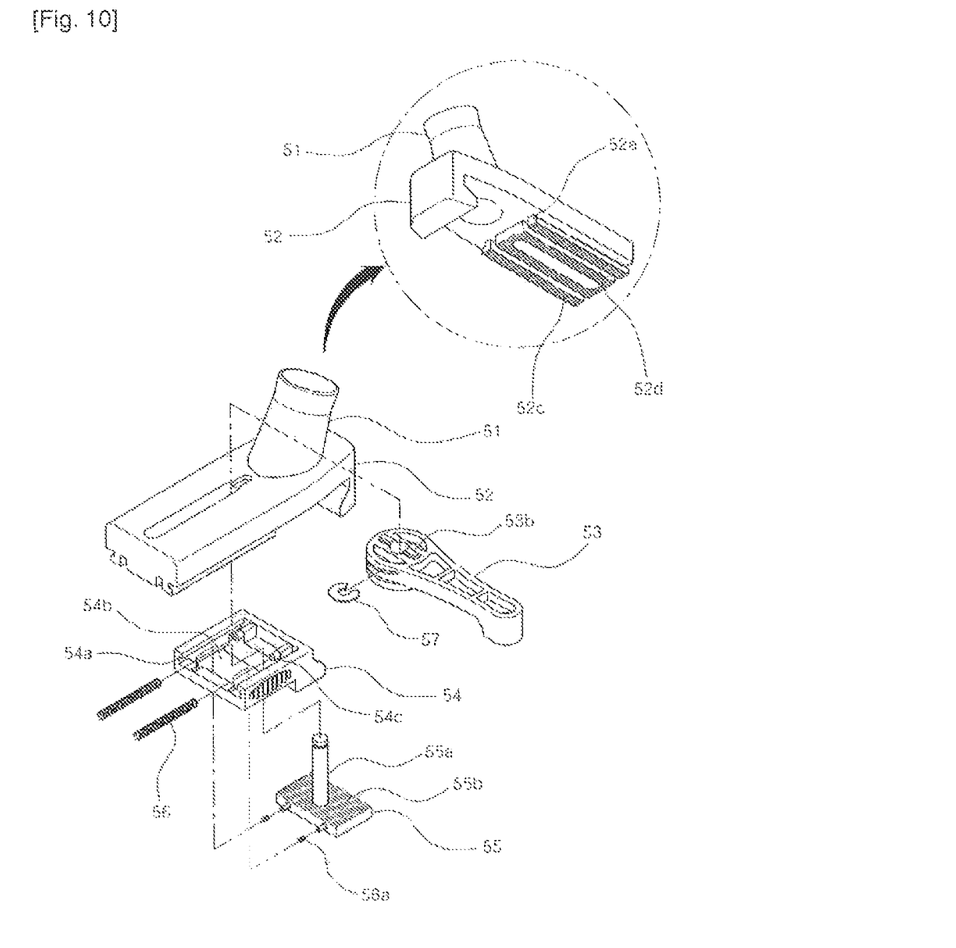
FIG. 10 is an assembled structure view of a main holder of the present invention.

As shown in FIGS. 5 and 9, when only the angle of the adjustor 30 is to be converted leftward and rightward after the angle of the suction head 20 as well as the adjustor 30 is regulated and the main holder 50 is fixed to a rail of an operation table, the adjustor 30 is engaged with the handle 40 to be prevented from being withdrawn from the handle 40 even while rotating so that the adjustor 30 can be moved while the block bodies of the adjustor 30 are not separated. In this engaged state, the operating body 44 rotatably mounted to the fixing body 43 is engaged with the handle 40 so as not to be rotated if the handle 40 is rotated leftward and rightward. While the fixing body 43 is introduced into the recessed operating shaft 42, the head 43a of the fixing body 43 has various angles so that the operating body 44 is rotated at the same time if the handle 40 is rotated, and if the fixing body 43 rotatably introduced into the operating body 44 is moved forward and rearward, the handle 40 is moved forward by pulling the wire 100 and the recessed operating shaft 42 is moved forward at the same time.

Then, a protruding shaft 42a inclinedly protruding to the front side of the recessed operating shaft 42 is fixed or released as a recessed surface 51a of a holder connecting portion 51 and an attaching surface 45a of a holder interrupting portion 45 are attached to or separated from each other while the holder interrupting portion 45 is introduced into the holder connecting portion 51 connecting the main holder 50 and the handle holder 41.

For the attaching and releasing operation, an inclined surface 42b is formed in the protruding shaft 42a to be inclined to one side, and a stopping step 45a for preventing a slide surface 45b inclined formed in the holder interrupting portion 45 and the protruding shaft 42a from being withdrawn from each other is formed in the holder interrupting portion 45 so that the holder interrupting portion 45 can be attached to or released from the holder connecting portion 51 while the holder interrupting portion 45 is raised and lowered.

Thus, the handle holder 41 is engaged with the holder connecting portion 51 so that the direction of the handle holder 41 can be fixed or converted as the handle holder 41 is loosened from or fastened to the holder interrupting portion.

As shown in FIGS. 10 to 13, the holder connecting portion 51 connected to the handle holder 41 protrudes from an upper side of the body 52, a lever 53 is formed at an upper side of the body 52, and a slider 54 for fixing the main holder 50 to a rail and a connecting body 55 for fixing the slider 54 without separating the slider 54 is coupled to the lever 53 on a lower side of the body 52, so that the main holder 50 is fixed or released as the connecting body 55 is attached to or separated from the body 52 through manipulation of the lever 53.

Then, the slider 54 is moved leftward and rightward while a stopping step 54a is inserted into a slide groove 52a and is not withdrawn to a lower side, is moved leftward and rightward to one side by an external force in a state where the slider 54 is always pushed to an opposite side, and is moved by the connecting body 55 inserted into an opening 54b of the slider 54 to guide the leftward and rightward movement of the slider 54, and the connecting body 55 is fixed by a snap ring 57 in a state where the connecting shaft 55a is inserted into the shaft groove 53a of the lever 53 to be moved along an opening groove 52b of the body 52.

Then, the spring 56 is introduced into the rail 52d formed on opposite sides while an uneven surface 52c of the body 52 protrudes, a stopping step 52e is formed at a tip end of the rail 52d to prevent the spring 56 inserted into the rail 52d from being separated, and the spring 56 is fitted with the insertion boss 54c formed in the slider 54 to reinforce a fixing force.

Figure 11:
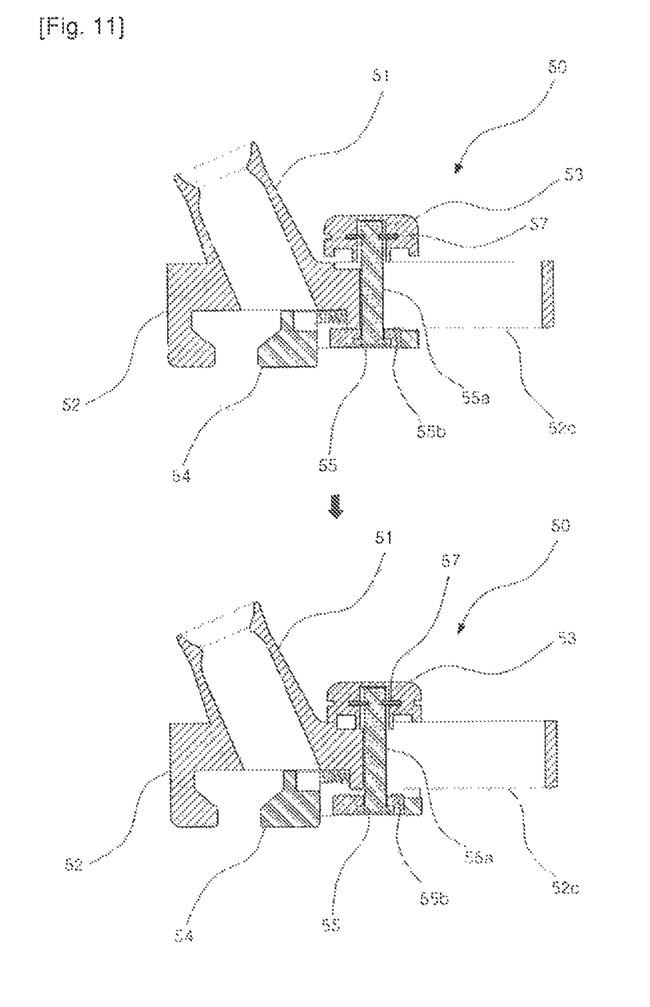
FIG. 11 an operation state view according to manipulation of a lever of the present invention.
Figure 12:
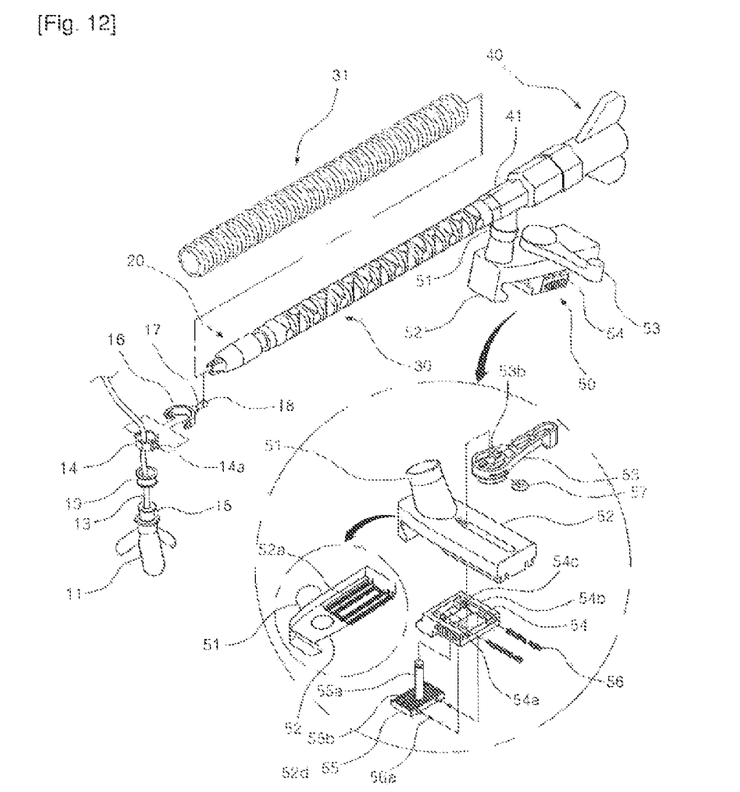
FIG. 12 is an entire assembly view of the main holder of the present invention.

An inclined boss 53b is formed in the lever 53 so that if the lever 53 is rotated to one side, the connecting body 55 is raised by the inclined boss 53b and the uneven surface 55b of the connecting body 55 and the uneven surface 52c of the body are engaged with each other to be fixed while an interval thereof is adjusted.

Figure 13:
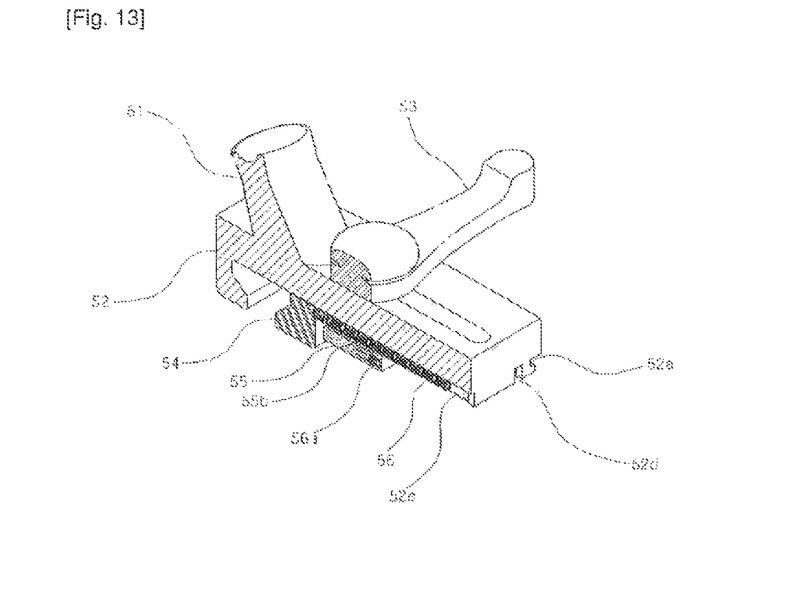
FIG. 13 is a state view in which a connecting body is coupled to a main holder body of the present invention.

Then, the connecting body 55 is connected to the slider 54 by the spring 56a so that a resilient force for easy operation of the connecting body 55 is secured while the connecting body 55 is inserted into the opening 54b of the slider 54, and the spring prevents separation due to the fixing boss and the insertion groove.

The invention claimed is:

1. A heart stabilizer comprising:
   a suction unit (10) adapted to fixedly attach to a surface of a heart through a suction operation of an intake tube (13) connected to an upper side of the suction unit (10);
   a suction head (20) connecting the suction unit (10) and an adjustor (30) to adjust and fix an upward, downward, leftward, and rightward movement range of the suction unit (10);
   an adjustor (30) for fixing the adjusted state through manipulation of a handle (40) while guiding the adjusted movement range of the suction head (20);
   the handle (40) mounted to a rear end of the adjustor (30) so as to be connected to the adjustor (30) to position the suction head (20) as well as the adjustor (30) through fastening and releasing the adjustor (30); and
   a main holder (50) connected to a tip end and a rear end of the handle (40) so as to extend to the adjustor (30) and adapted to fix the adjustor (30) to a rail of an operating table,
   wherein auxiliary radial gas passages (13b) are formed on an inner wall of a gas passage (13a) of the intake tube (13) so as to be recessed to prevent the intake tube (13) from failing to properly perform an intake operation when the intake tube (13) is bent during an operation due to twisting thereof generated when a position of the intake tube (13) is changed variously.

2. The heart stabilizer of claim 1, wherein a rotary shaft (15) is formed at an upper side of the suction unit (10) and a washer (14) is fitted with the rotary shaft (15) so that the rotary shaft (15) is rotated to finely change a location at which a branch tube (11) of the suction unit (10) is attached to a surface of the heart when an angle of the suction unit (10) is adjusted by the suction head (20), and a fixing boss (14a) is formed in the washer (14) after the washer (14) is fitted with the rotary shaft (15), and is inserted into a boss hole (16a) of a connecting body (16) inserted into the suction head (20).

3. The heart stabilizer of claim 2, wherein the washer (14) is connected to the rotary shaft (15) by means of a separate packing (19) to prevent the washer (14) from damaging the suction unit (10).

4. The heart stabilizer of any one of claims 2 to 3, wherein the suction head (20) connected to a connecting ball (18) of a connecting shaft (17) of the connecting body (16), in which the connecting shaft (17) has a predetermined length, is connected to the adjustor (30) having block bodies to adjust a bending angle of the adjustor (30) by pulling and releasing a wire (100)through manipulation of the handle (40), the adjustor (30) is configured by assembling three block bodies (32) which are coupled to each other by a vinyl cover generally contracted by heat to prevent dust from being put between assembly apertures when the adjustor (30) is exposed to the outside, and a bellows tube (31) is coupled between the suction head (20)and the main holder (50) outside the adjustor (30) to be prevented from being arbitrarily separated to prevent introduction of foreign substances so that a function of the adjustor (30) is smoothly performed by preventing dust from being put between the apertures of the block bodies constituting the adjustor (30) by using the vinyl cover.

5. The heart stabilizer of claim 4, wherein a suction opening (12) is formed on an inner side of a recessed opening (12-1) recessed in a step structure to prevent clogging due to the epidermis when a suction operation is performed toward an inner side of the branch tube (11) branched to three directions so that the suction unit (10) is firmly attached to a surface of the heart through the suction operation of the intake tube (13) connected to the upper side of the suction unit (10).

6. The heart stabilizer of claim 4, wherein the suction unit (10a) is curved to one side edge in a straight shape and is curved in a state where the intake tube (13) is linearly introduced into a plurality of suction openings (12a) arranged in a row so that the suction openings (12a) are located at different locations of the recessed opening (12-1).

7. The heart stabilizer of claim 4, wherein the suction head (20) comprises:
   a pressing shaft (24) configured to resiliently guide fixing and releasing of the connecting body (16);
   an accommodating cap (21) configured to accommodate the pressing shaft (24) while accommodating the connecting body (16) to prevent the connecting body (16) from being withdrawn to the front side;
   an operating shaft (25) configured to release the pressing shaft guiding an operation (24) accommodated in and the accommodating cap (21) while accommodating the accommodating cap (21);
   an operating cap (22) configured to accommodate a slide boss (23a) of an operating body (23) in which the operating shaft (25) is accommodated and which is moved forward and rearward by pulling and releasing the wire (100) while being engaged with the slide boss (23a); and
   a fixing body (26) having a guide groove (26a) in which the slide boss (23a) of the operating body (23) engaged with the operating cap (22) to be accommodated is raised and lowered.

8. The heart stabilizer of claim 4, wherein the adjustor (30) comprises:
   disk bodies (31, 32) side surfaces of which are engaged with a recess (33) and a protrusion (34); and
   inclined surfaces (38) formed at opposite sides of the adjustor (30) such that the adjustor (30) is bent and maintained at a predetermined angle by bending the disk bodies (31,32) with a cylindrical body (36) while taking curved recesses (35) formed on rear surfaces of the disk bodies (31,32) as borders, and
   wherein the cylindrical body (36) a substantially half of which is inserted into and attached to the curved recess (35) are connected between the disk bodies engaged with each other in perpendicular to each other continuously, a wire (100) is connected through a hole (37) punched at a center of the cylindrical body (36), and one end of the wire (100) fixedly extends to the handle (40) located at a rear side of the main holder (50) while being fixed to the operating shaft (25) of the suction head (20).

9. The heart stabilizer of claim 4, wherein the handle (40) comprises:
   a handle holder (41) connecting the adjustor (30) and the handle (40);
   a fixing body (43) by which one end of the wire (100) is fixed to an interior of the handle holder (41);
   a recessed operating shaft (42) into which the fixing body (43) is introduced; and an operating body (44) engaged with and coupled to the handle (40) to be prevented from being withdrawn while rotating in a state where the recessed operating shaft is introduced, and mounted such that the fixing body (43) is rotated in the handle (40) if the handle (40) is rotated leftward and rightward in the coupled state, and wherein the operating body (44) is engaged with the handle (40) so as not to be rotated, a head (43a) of the fixing body (43) is formed to be polygonal in a state where the fixing body (43) is introduced into the recessed operating shaft (42) such that if the handle (40) is rotated, the operating body (44) is rotated at the same time, and if the fixing body (43) rotatably introduced into the operating body (44) is moved forward and rearward, the handle (40 is moved forward by pulling the wire (100), and then if the recessed operating shaft (42) is moved forward, a protruding shaft (42a) inclinedly protruding to a front side of the recessed operating shaft (42) is fixed and separated as a recessed surface (51a) of a holder connecting portion (51a) and an attaching surface (45a) of a holder interrupting portion (45) are attached to or separated from each other in a state where the holder interrupting portion (45) is introduced into the holder connecting portion (51) connecting the main holder (51) and the handle holder (41).

10. The head stabilizer of claim 4, wherein the holder connecting portion (51) connected to the handle holder (41) protrudes from an upper side of the body (52), a lever (53) is formed at an upper side of the body (52), and a slider (54) for fixing the main holder (50) to a rail and a connecting body (55) for fixing the slider (54) without separating the slider (54) is coupled to the lever (53) on a lower side of the body (52), so that the main holder (50) is fixed or released as the connecting body (55) is attached to or separated from the body (52) through manipulation of the lever (53).

11. The heart stabilizer of claim 10, wherein the slider (54) is moved leftward and rightward while a stopping step (54a) is inserted into a slide groove (52a) and is not withdrawn to a lower side, is moved leftward and rightward to one side by an external force in a state where the slider (54) is always pushed to an opposite side, and is moved by the connecting body (55) inserted into an opening (54b) of the slider (54) to guide the leftward and rightward movement of the slider (54), and the connecting body (55) is fixed by a snap ring (57) in a state where the connecting shaft groove (53a) of the lever (55a) is inserted into the shaft (53) to be moved along an opening groove (52b) of the body (52).

* * * * *